United States Patent [19]

Cassinelli et al.

[11] 4,322,412
[45] Mar. 30, 1982

[54] ANTHRACYCLINE GLYCOSIDES, THEIR PREPARATION, USE AND COMPOSITIONS THEREOF

[75] Inventors: Giuseppe Cassinelli, Voghera; Salvatore Forenza, Milan; Maria C. Ripamonti, Monza; Daniela Ruggieri, Milan, all of Italy

[73] Assignee: Farmitalia Carlo Erba S.p.A., Milan, Italy

[21] Appl. No.: 168,157

[22] Filed: Jul. 14, 1980

[30] Foreign Application Priority Data

Jul. 4, 1979 [GB] United Kingdom ............... 23225/79

[51] Int. Cl.³ .................... A61K 31/71; C07H 15/24
[52] U.S. Cl. .................................... 424/180; 536/17 A
[58] Field of Search ..................... 424/180; 536/17 A

[56] References Cited

U.S. PATENT DOCUMENTS 4,039,663  8/1977  Arcamone et al. ............... 536/17 A
4,183,919  1/1980  Cassinelli et al. ................ 536/17 A
4,191,756  3/1980  Masi et al. ....................... 536/17 A

OTHER PUBLICATIONS

Arcamone et al., "Tetrahedron Letters", No. 30, pp. 3353–3356, 1968.

*Primary Examiner*—Johnnie R. Brown

*Attorney, Agent, or Firm*—Berger & Palmer

[57] ABSTRACT

There are disclosed compounds which exhibit anti-tumor activity. These compounds are of the formula I:

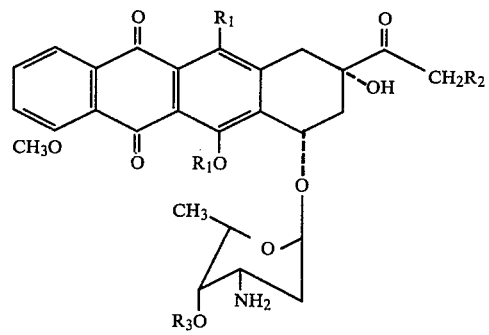

wherein $R_1$ is hydrogen, hydroxy or methoxy, $R_2$ is hydrogen or hydroxy, and each of $R_3$ and $R_4$ independently is hydrogen or methyl, with the proviso that $R_3$ and $R_4$ are not simultaneously hydrogen, and pharmaceutically acceptable acid addition salts thereof. Also disclosed are processes for producing and using said compounds and therapeutic compositions containing same.

12 Claims, No Drawings

ANTHRACYCLINE GLYCOSIDES, THEIR PREPARATION, USE AND COMPOSITIONS THEREOF

CROSS REFERENCE TO RELATED APPLICATIONS

This application is related to and incorporates by reference the contents of U.S. Pat. No. 3,803,124; Belgian Pat. No. 864,336; and British patent application No. 7903901 (2016005 A), all of which are owned by the unrecorded assignee hereof.

BACKGROUND OF THE INVENTION

1. Field of the Invention

The present invention relates to anthracycline antitumor glycosides which are daunorubicin and doxorubicin analogues, methods for their preparation, compositions containing same and the use thereof as well as certain novel intermediates used in their preparation.

2. The Prior Art

Daunorubicin (daunomycin) and doxorubicin (adriamycin) are both well known anthracycline antitumor glycosides, and both their preparation and use are amply described in the prior art. Some of the compounds which are prepared by the process of the invention are known. Thus, 11-O-methyl-daunorubicin (VI) and 11-O-methyl-doxorubicin (VII) are disclosed in Belgian Pat. No. 864,336. One of the starting materials for the process of the invention, namely, 11-deoxy-daunorubicin (XVI) is a natural anthracycline, and is described in British application No. 7903901. Finally, a starting material for another aspect of the invention, namely N-trifluoroacetyl-daunorubicin (XI) is described in U.S. Pat. No. 3,803,124.

SUMMARY OF THE INVENTION

The present invention provides, in one aspect thereof, a new class of anthracycline glycoside antibiotics of the formula I

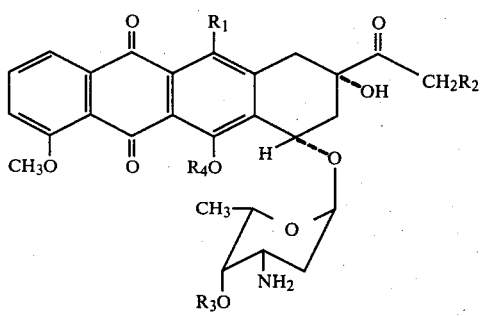

wherein $R_1$ is hydrogen, hydroxy or methoxy, $R_2$ is hydrogen or hydroxy and each of $R_3$ and $R_4$ is independently selected from the group consisting of hydrogen and methyl, with the proviso that $R_3$ and $R_4$ are not simultaneously hydrogen, and the pharmaceutically acceptable acid addition salts thereof.

Clearly, when $R_2$ is hydrogen the compounds are daunorubicin analogues and when $R_2$ is hydroxy they are doxorubicin analogues. Particular reference will be made to 4'-O-methyl-11-deoxy-daunorubicin (II), 4'-O-methyl-11-deoxy-doxorubicin (III), 4',6-di-O-methyl-11-deoxy-daunorubicin (IV), 4',6-di-O-methyl-11-deoxy-doxorubicin (V), 11-O-methyl-daunorubicin (VI), 11-O-methyl-doxorubicin (VII), 4',11-di-O-methyl-daunorubicin (VIII) and 4',11-di-O-methyl-doxorubicin (IX), which are among the more important compounds of formula I. Each of those compounds has the following substituents in formula (I):

(II) $R_1=R_2=R_4=H$; $R_3=CH_3$
(III) $R_1=R_4=H$; $R_2=OH$; $R_3=CH_3$
(IV) $R_1=R_2=H$; $R_3=R_4=CH_3$
(V) $R_1=H$; $R_2=OH$; $R_3=R_4=CH_3$
(VI) $R_1=OCH_3$; $R_2=R_3=R_4=H$
(VII) $R_1=OCH_3$; $R_2=OH$; $R_3=R_4=H$
(VIII) $R_1=OCH_3$; $R_2=R_4=H$; $R_3=CH_3$
(IX) $R_1=OCH_3$; $R_2=OH$; $R_3=CH_3$; $R_4=H$

As noted previously, compounds (VI) and (VII) are disclosed in Belgian Pat. No. 864,336.

In another aspect thereof, the invention provides a process for the preparation of 4'-O-methyl-11-deoxy-daunorubicin (II) and 4',6-di-O-methyl-11-deoxy-daunorubicin (IV). The process comprises subjecting 11-deoxy-daunorubicin (XVI), a natural anthracycline described in British patent application No. 7903901 (2016005 A) to N-trifluoroacetylation to form 11-deoxy-N-trifluoroacetyl-daunorubicin (X), methylating compound (X) with methyl iodide in the presence of silver (I) oxide, to form a mixture of 4'-O-methyl-11-deoxy-N-trifluoroacetyl-daunorubicin (XII) and 4',6-di-O-methyl-11-deoxy-N-trifluoroacetyl-daunorubicin (XIII) and removing the N-trifluoroacetyl protecting groups therefrom by mild alkaline hydrolysis. According to a different aspect of the process of the invention, 11-O-methyl-daunorubicin (VI) and 4',-11-di-O-methyl-daunorubicin (VIII) are prepared from daunorubicin (XVII) instead of 11-deoxy-daunorubicin (XVI). In this aspect of the process, daunorubicin (XVII) is subjected to N-trifluoroacetylation, methylation and de-N-trifluoroacetylation.

These processes are illustrated with reference to the formulae and reaction schemes set forth below

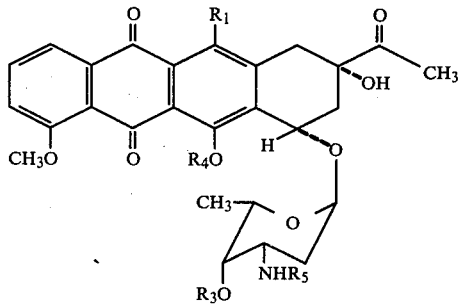

XVI 11-deoxy-daunorubicin
  $R_1=R_3=R_4=R_5=H$
XVII daunorubicin
  $R_1=OH$, $R_3=R_4=R_5=H$
X 11-deoxy-N-trifluoroacetyl-daunorubicin
  $R_1=R_3=R_4=H$, $R_5=COCF_3$
XI N-trifluoroacetyl-daunorubicin
  $R_1=OH$, $R_3=R_4=H$, $R_5=COCF_3$
XII 4'-O-methyl-11-deoxy-N-trifluoroacetyl-daunorubicin
  $R_1=R_4=H$, $R_3=CH_3$, $R_5=COCF_3$
XIII 4',6-di-O-methyl-11-deoxy-N-trifluoroacetyl-daunorubicin
  $R_1=H$, $R_3=R_4=CH_3$, $R_5=COCF_3$
XIV 11-O-methyl-N-trifluoroacetyl-daunorubicin $R_1$=OCH$_3$, $R_3$=R$_4$=H, $R_5$=COCF$_3$
XV 4'-11-di-O-methyl-N-trifluoroacetyl-daunorubicin
$R_1$=OCH$_3$, $R_3$=CH$_3$, $R_4$=H, $R_5$=COCF$_3$

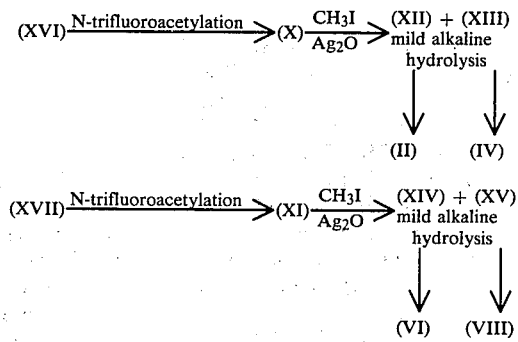

Clearly, since N-trifluoroacetyl-daunorubicin (XI) itself is a known compound (United States Pat. No. 3,803,124), the preparation of compounds (VI) and (VIII) may commence from that compound, thereby omitting the first step shown in the above reaction scheme, namely, the N-trifluoroacetylation of daunorubicin (XVII).

The daunorubicin analogues II, IV, VI, and VIII can be converted to the corresponding doxorubicin analogues III, V, VII, and IX, according to the method described in U.S. Pat. No. 3,803,124 by 14-bromination and hydrolysis. This conversion is also within the scope of the process according to the invention.

In another aspect, the invention provides a group of novel N-trifluoroacetyl intermediates obtained during the preparation of the ultimate products. These intermediates have the following formula:

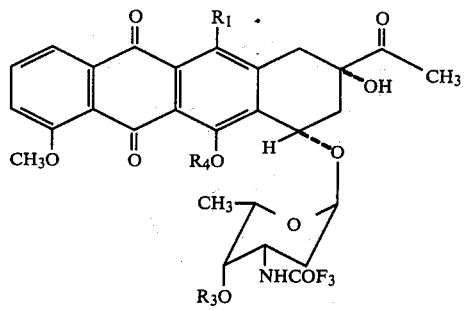

wherein $R_1$ is hydrogen or methoxy; $R_3$ is hydrogen or methyl and $R_4$ is hydrogen or methyl.

In still further aspects thereof, the invention provides compositions containing and methods for using the compounds of Formula I in treating certain mammalian tumors by administering a therapeutically effective amount of a compound of Formula I, preferably in the form of a composition containing such compound, to a mammal afflicted with a tumor such as P$_{388}$ leukemia.

DESCRIPTION OF THE PREFERRED EMBODIMENTS

The invention is illustrated in detail by the following examples showing the preparation of the compounds according to the invention.

EXAMPLE 1

Preparation of 4'-O-methyl-11-deoxydaunorubicin (II).

A solution of 0.600 g (1.09 mmoles) of 11-deoxydaunorubicin hydrochloride in 60 ml of anhydrous chloroform was treated with 2.0 ml of trifluoroacetic anhydride at 0° C., with stirring. After 1 hour the resulting solution was evaporated to dryness under reduced pressure, leaving a residue which was then suspended in 50 ml of water, adjusted to pH 8 with saturated aqueous sodium bicarbonate and extracted with two 50 ml portions of chloroform. The organic phase was separated, and after being dried over anhydrous sodium sulphate was reduced to a small volume; about 5 ml. To the solution, 100 ml of methanol were added. After 2 hours the resulting solution was evaporated to dryness. The residue was dissolved in the smallest amount of chloroform required to effect solution, and upon the addition of sufficient petroleum ether 0.630 g; 1.05 mmoles of 11-deoxy-N-trifluoroacetyl-daunorubicin (X) precipitated as a yellow crystalline powder: m.p. 147°-149° C.; $[\alpha]_D$=+140° (c=0.1 in CH$_3$OH); m/e 607 (M+). The p.m.r. spectrum (CDCl$_3$) shows absorptions at 129 (d, CH$_3$—C—5'), 2.37 (s, CH$_3$—CO), 4.03 (s, C—4—OCH$_3$), 5.22 (broad signal, C—7—H), 5.47 (broad signal, C—1'—H) and 13.80δ (s, C—6—OH).

Compound X (0.650 g; 1.07 mmoles) was treated with 50 ml of methyl iodide in the presence of 1.3 g of silver oxide at 40° C. for 2 hours with stirring. The reaction mixture was filtered, and the solid precipitate was washed with three 100 ml portions of chloroform. The combined chloroform filtrates were evaporated to dryness under reduced pressure. The crude reaction mixture was purified on a silica gel column, eluting with a chloroform/methanol gradient solution, to afford 4'-O-methyl-11-deoxy-N-trifluoroacetyl-daunorubicin (XII) (0.250 g; 0.41 mmole) and 4',6-di-O-methyl-11-deoxy-N-trifluoroacetyl-daunorubicin (XIII) (0.200 g; 0.31 mmole).

Compound XII, which was eluted with chloroform has a m.p. of 128°-131° C.; $[\alpha]_D$=+140° (c=0.1 in CH$_3$OH); m/e 621 (M+). The p.m.r. spectrum (CDCl$_3$) shows absorptions at 1.37 (d, CH$_3$—C—5'), 2.40 (s, CH$_3$—CO), 3.57 (s, C—4'—OCH$_3$), 4.08 (s, C—4—OCH$_3$), 5.30 (broad signal, C—7—H), 5.53 (broad signal, C—1'—H) and 13.70δ (s, C—6—OH).

Compound XIII which was eluted with chloroform: methanol 99:1 has a m.p. of 124°-127° C.; $[\alpha]_D$=+25° (c=0.1 in CH$_3$OH); m/e 635 (M+). The p.m.r. spectrum (CDCl$_3$) shows absorption at 1.37 (d, CH$_3$—C—5'), 2.38 (s, CH$_3$CO), 3.55 (s, C—4'—OCH$_3$), 4.02 (s, two aromatic OCH$_3$), 5.33 (broad signal, C—7—H) and 5.43δ (broad signal, C—1'—H).

A solution of 0.230 g; 0.37 mmol of compound XII in 25 ml of 0.25 M aqueous sodium hydroxide was kept for 30 minutes at room temperature, under stirring. The resulting solution was diluted with 30 ml of water, adjusted to pH 3 with 0.25 M hydrochloric acid, and extracted with chloroform to eliminate impurities. The aqueous phase after being adjusted to pH 8.2 with saturated aqueous sodium bicarbonate was extraced with three 100 ml portions of chloroform. The combined organic (chloroform) extracts were dried over anhydrous sodium sulphate, concentrated to a small volume and acidified to pH 4.5 with 0.5 M methanolic hydrogen chloride. Addition of sufficient petroleum ether precipitated 4'-O-methyl-11-deoxy-daunorubicin (II) as the hydrochloride (0.200 g; 0.36 mmole): m.p. 194°–197° C. (with decomposition); mass spectrum, in field absorption, m/e 525 (M+). The I.R. spectrum (KBr) shows absorptions at 1710 ($COCH_3$), 1670, 1620, and 1590 $cm^{-1}$ (quinone bands). The UV-Visible spectrum (in $CH_3OH$) shows absorption maxima at 227, 260, 284 (sh), 417, and 434 (sh) nm ($E_{1cm}^{1\%}$ 500, 330, 173, 167 and 146).

EXAMPLE 2

4'-O-methyl-11-deoxy-doxorubicin (III).

A solution of 0.180 g; 0.34 mmole of 4'-O-methyl-11-deoxy-daunorubicin (II) in 2.5 ml of anhydrous methanol, 6.9 ml of anhydrous dioxan and 0.18 ml of ethyl orthoformate was treated with 0.7 ml of a 1.3 M solution of bromine in chloroform. After 2 hours, at 10° C., the resulting solution was poured into 18 ml of petroleum ether and 36 ml of diethyl ether. The precipitate was filtered off, washed with diethyl ether and dried under vacuum.

The thus obtained product was dissolved in 5.8 ml of acetone and 5.8 ml of 0.25 M aqueous hydrogen bromide were added thereto. The reaction mixture was kept overnight at room temperature.

To the reaction mixture there were added 1.35 ml of 20% aqueous sodium formate. The solution was kept at 30° C. for 24 hours. The resulting mixture was extracted with chloroform to eliminate impurities, then adjusted to pH 7.5 with saturated aqueous sodium bicarbonate solution and extracted with chloroform. The organic phase was washed with water, dried over anhydrous sodium sulphate, taken up in n-propanol and brought to a small volume. The addition of 2.1 N methanolic hydrogen chloride and of sufficient diethyl ether to cause precipitation afforded 0.135 g; 0.23 mmole of 4'-O-methyl-11-deoxy-doxorubicin (III) as the hydrochloride: m.p. 189°–193° C., mass spectrum, in field desorption, m/e 541 (M+). The I.R. spectrum (KBr) shows absorptions at 1725 ($COCH_2OH$), 1670, 1630, and 1590 $cm^{-1}$ (quinone bands). The UV-Visible spectrum (in $CH_3OH$) shows absorption maxima at 227, 259, 285 (sh), 418 and 436 (sh) ($E_{1\ cm}^{1\%}$ 673, 424, 221, 177 and 151).

EXAMPLE 3

4',6-di-O-methyl-11-deoxy daunorubicin (IV).

Alkaline hydrolysis of 4',6-di-O-methyl-11-deoxy-N-trifluoroacetyl-daunorubicin (XIII) (0.180 g; 0.28 mmole), following the procedure described in Example 1, yielded 4',6-di-O-methyl-11-deoxy-daunorubicin as the hydrochloride (IV) (0.030 g; 0.05 mmole): m.p. 182°–185° C. (with decomposition); mass spectrum, in field desorption, m/e 539 (M+). The I.R. spectrum (KBr) shows absorptions at 1710 ($COCH_3$), 1670 and 1590 $cm^{-1}$ (quinone bands). The UV-Visible spectrum (in $CH_3OH$) shows absorption maxima at 223, 260 and 382 nm ($E_{1\ cm}^{1\%}$ 353, 326, and 109).

EXAMPLE 4

Preparation of 11-O-methyl-daunorubicin (IV).

N-Trifluoroacetyl-daunorubicin (XI) (1.5 g; 2.40 mmoles) was methylated with 60 ml of methyl iodide in the presence of 10 g of silver oxide following the procedure described in Example 1. Purification of the crude reaction mixture on a silica gel column using chloroform as eluant, yielded 11-O-methyl-N-trifluoroacetyl-daunorubicin (XIV) (0.842 g; 1.32 mmoles) as the major product along with 4', 11-di-O-methyl-N-trifluoroacetyl-daunorubicin (XV) (0.270 g; 0.415 mmole).

Compound XIV has a m.p. of 136°–138° C.; $[\alpha]_D = +140°$ (c=0.05 in $CH_3OH$); m/e 637 (M+). The p.m.r. spectrum ($CDCl_3$) shows absorptions at 1.32 (d, $CH_3$—C—5'), 2.39 (s, $CH_3CO$), 3.85 (s, C—11—$OCH_3$), 4.03 (s, C—4—$OCH_3$), 5.23 (broad signal, C—7—H), 5.45 (broad signal, C—1'—H) and 13.95δ (s, C—6—OH).

Compound XV has a m.p. of 103°–105° C.; $[\alpha]_D = +80°$ (c=0.05 in $CH_3OH$); m/e 651 (M+). The p.m.r. spectrum ($CDCl_3$) shows absorptions at 1.34 (d, $CH_3$—C—5'), 2.39 (s, $CH_3CO$), 3.53 (s, C—4'—$OCH_3$), 3.84 (s, C—11—$OCH_3$), 4.03 (s, C—4—$OCH_3$), 5.23 (broad signal, C—7—H), 5.48 (broad signal, C—1'—H), and 13.93δ (C—6—OH).

To a solution of 0.400 g; 0.628 mmol of compound XIV in 20 ml of acetone there were added dropwise 40 ml of 0.12 M aqueous sodium hydroxide. The mixture was stirred at 0° C. for 3 hours. The work-up is carried out according to the procedure described in Example 1 and yielded 0.250 g (0.44 mmole) of 11-O-methyl-daunorubicin as the hydrochloride (VI): m.p. 186°–187° C. (with decomposition); mass spectrum, in field desorption, m/e 541 (M+). The I.R. spectrum (KBr) shows absorptions at 1710 ($COCH_3$), 1670, 1620 and 1590 $cm^{-1}$ (quinone bands). The UV-Visible spectrum (in $CH_3OH$) shows absorption maxima at 230, 252, 281 (sh), 428 and 442 (sh) nm ($E_{1\ cm}^{1\%}$ 593, 355, 145, 180, and 175).

EXAMPLE 5

4', 11-di-O-methyldaunorubicin (VIII)

Alkaline hydrolysis of 4', 11-di-O-methyl-N-trifluoroacetyl-daunorubicin (XV) (0.250 g; 0.384 mmole), following the procedure described in Example 4, yielded 4', 11-di-O-methyl daunorubicin as the hydrochloride (VIII) (0.140 g; 0.237 mmole): m.p. 192°–194° C. (with decomposition); mass spectrum, in field desorption, m/e 555 (M+). The I.R. spectrum (KBr) shows absorptions at 1710 ($COCH_3$), 1670, 1620, and 1590 $cm^{-1}$ (quinone bands). The UV-Visible spectrum (in $CH_3OH$) shows absorption maxima at 230, 252, 284 (sh), 428 and 442 (sh) nm ($E_{1\ cm}^{1\%}$ 598, 430, 159, 159 and 159).

BIOLOGICAL ACTIVITY

Antitumor Activity

Several of the new compounds of the invention were tested on HeLa cells cloning efficiency in vitro and on P-388 ascitic leukemia in mice, in comparison with daunorubicin and doxorubicin.

From the data reported in Table 1, it can be seen that the 11-deoxy-4'-O-methyl derivatives of daunorubicin (II) and of doxorubicin (III) are less cytotoxic than their respective parent compounds. Accordingly, they were also less toxic in vivo, and at the maximal tolerated dose exhibited an antitumor activity comparable to that of the parent compounds (Table 2). Of particular interest is compound III which showed both a wide range of active and non-toxic doses.

Compounds VI and VIII are markedly less cytotoxic than are their parent compounds (Table 1) and when treated in vivo even at a dose of 200 mg/kg, they were not toxic and displayed an antitumor activity comparable to that of daunorubicin in the same experiment (Table 2).

TABLE 1

Effect on HeLa Cells Cloning Efficiency In Vitro[a]

| Compound | $ID_{50}$ (ng/ml) |
| --- | --- |
| Daunorubicin . HCl | 7.2 |
| Doxorubicin . HCl (adriamycin) | 9.5 |
| 4'-O-methyl-11-deoxy-daunorubicin . HCl (II) | 66 |
| 4'-O-methyl-11-deoxy-doxorubicin . HCl (III) | 22 |
| 4'-6-di-O-methyl-11-deoxy-daunorubicin . HCl (IV) | 1000 |
| 11-O-methyl-daunorubicin . HCl (VI) | 400 |
| 4'-11-di-O-methyl-daunorubicin . HCl (VIII) | 500 |

[a]HeLa cells were exposed to the test compounds for 24 hours, then plated. The number of colonies was evaluated 5 days later.

TABLE 2

Antitumor Activity on Ascitic P 388 Leukemia in Mice

| Compound | Dose[a] mg/kg | T/C[b] % | Toxic Deaths[c] | |
| --- | --- | --- | --- | --- |
| Daunorubicin . HCl[d] | 2.9 | 175,122 | 0/10, | 0/8 |
| | 4.4 | 180,122 | 3/10, | 0/6 |
| | 6.6 | 165,122 | 8/10, | 0/6 |
| 4'-O-methyl-11-deoxy-daunorubicin . HCl (II) | 25 | 180 | 0/9 | |
| | 50 | 225 | 1/9 | |
| 4'-11-di-O-methyl-daunorubicin . HCl (VIII) | 100 | 111 | 0/6 | |
| | 200 | 122 | 0/6 | |
| 11-O-methyl-daunorubicin . HCl (VI) | 100 | 111 | 0/4 | |
| | 200 | 122 | 0/3 | |
| Doxorubicin . HCl (Adriamycin) | 4.4 | 219 | 0/8 | |
| | 6.6 | 223 | 0/8 | |
| | 10.0 | 180 | 4/8 | |
| 4'-O-methyl-11-deoxy-doxorubicin . HCl (III) | 6.6 | 195 | 0/8 | |
| | 10 | 209 | 0/8 | |
| | 15 | 238 | 0/7 | |
| | 22.5 | 214 | 0/10 | |

[a]Mice were treated i.p. on day 1 after tumor cells inoculation.
[b]Median survival time of treated mice/median survival time of control mice × 100.
[c]Evaluated on the basis of macroscopic autoptic findings.
[d]Data of two separate experiments.

Variations and modifications can, of course, be made without departing from the spirit and scope of the invention.

Having thus described our invention what we desire to secure by Letters Patent and hereby claim is:

1. A compound of the formula:

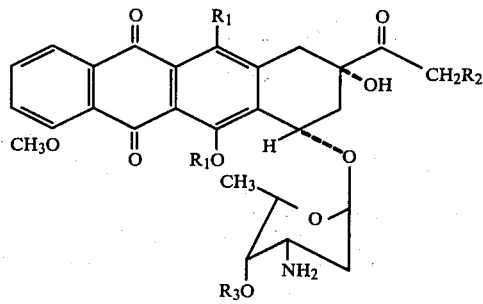

wherein $R_1$ is hydrogen or methoxy, $R_2$ is hydrogen or hydroxy, and each of $R_3$ and $R_4$ is independently hydrogen or methyl, with the proviso that $R_3$ and $R_4$ are not simultaneously hydrogen and the pharmaceutically acceptable acid addition salts thereof.

2. A compound according to claim 1, wherein $R_1$, $R_2$ and $R_4$ are hydrogen and $R_3$ is methyl.

3. A compound according to claim 1, wherein $R_1$ and $R_4$ are hydrogen, $R_2$ is hydroxy and $R_3$ is methyl.

4. A compound according to claim 1, wherein $R_1$ and $R_2$ are hydrogen and $R_3$ and $R_4$ are methyl.

5. A compound according to claim 1, wherein $R_1$ is methoxy $R_2$ and $R_4$ are hydrogen and $R_3$ is methyl.

6. A compound according to claim 1, wherein $R_1$ is hydrogen, $R_2$ is hydroxy and $R_3$ and $R_4$ are methyl.

7. A compound according to claim 1 wherein $R_1$ is methoxy, $R_2$ is hydroxy, $R_3$ is methyl and $R_4$ is hydrogen.

8. An N-trifluoracetylated compound of the formula

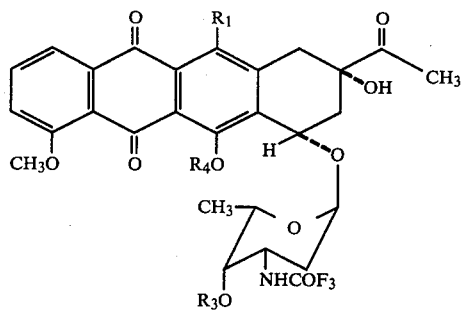

wherein $R_1$ is hydrogen or methoxy; $R_3$ is hydrogen or methyl and $R_4$ is hydrogen or methyl.

9. A process for the preparation of a compound as claimed in claim 1, said process comprising reacting 11-deoxydaunorubicin or daunorubicin with trifluoroacetic anhydride in anhydrous chloroform to obtain the corresponding N-trifluoroacetyl derivatives, separating said N-trifluoroacetyl derivatives from one another, separately subjecting each said N-trifluoroacetyl derivative to treatment with methyl iodide in the presence of silver oxide to form mixtures of 4'-O-methyl-11-deoxy-N-trifluoroacetyl-daunorubicin and 4'-6-di-O-methyl-11-deoxy-N-trifluoroacetyl-daunorubicin; and 11-O-methyl-daunorubicin and 4'-11-di-O-methyl-daunorubicin, separating the components of both said mixtures by chromatography on a silica gel column using a chloroform-methanol gradient solution, separately removing from each compound the N-trifluoroacetyl protecting groups by mild alkaline hydrolysis to obtain the free bases, treating said free bases with methanolic hydrogen chloride to form the hydrochlorides.

10. A process according to claim 9 and further comprising reacting the hydrochlorides with bromine in chloroform to form the respective 14-bromo-derivatives, hydrolyzing said 14-bromo derivatives at room temperature with sodium formate to form the corresponding doxorubicin derivatives and isolating same as the hydrochlorides.

11. A pharmaceutical composition for inhibiting the growth of transplanted P388 leukemia comprising a therapeutically effective amount of a compound according to claim 1 in combination with an inert carrier therefor.

12. A method of inhibiting the growth of transplanted P388 leukemia comprising intraperitoneally administering to a host afflicted therewith, a therapeutically effective amount of a compound as claimed in claim 1.

* * * * *